United States Patent [19]

Vermeulen

[11] Patent Number: 5,201,323

[45] Date of Patent: Apr. 13, 1993

[54] WIRE-GUIDED CYTOLOGY BRUSH

[75] Inventor: John P. Vermeulen, Jamaica Plain, Mass.

[73] Assignee: Brigham & Women's Hospital, Boston, Mass.

[21] Appl. No.: 659,631

[22] Filed: Feb. 20, 1991

[51] Int. Cl.$^5$ .............................................. A61B 10/00
[52] U.S. Cl. ..................................... 128/756; 128/749
[58] Field of Search ............... 128/749, 750, 751, 752, 128/753, 754, 755, 756, 757, 758, 759, 4; 604/158, 159, 161, 164, 165, 264, 1, 2, 3, 280, 283

[56] References Cited

U.S. PATENT DOCUMENTS

| | | | |
|---|---|---|---|
| 2,835,246 | 5/1958 | Boettger | 128/757 |
| 2,839,049 | 6/1958 | MacLean | 128/756 |
| 2,847,990 | 8/1958 | Ayre | 128/756 |
| 2,955,591 | 10/1960 | MacLean | 128/756 |
| 2,955,592 | 10/1960 | MacLean | 128/756 |
| 3,074,396 | 1/1963 | MacLean | 128/756 |
| 3,613,664 | 10/1971 | Willson et al. | 128/756 |
| 4,192,305 | 3/1980 | Seberg | 604/165 |
| 4,211,217 | 7/1980 | Gueret | 128/67 |
| 4,227,537 | 10/1980 | Suciu et al. | 128/756 |
| 4,230,123 | 10/1980 | Hawkins, Jr. | 128/658 |
| 4,235,244 | 11/1980 | Abele et al. | 128/749 |
| 4,324,262 | 4/1982 | Hall | 128/756 |
| 4,600,014 | 7/1986 | Beraha | 128/754 |
| 4,609,370 | 9/1986 | Morrison | 128/754 |
| 4,662,381 | 5/1987 | Inaba | 128/756 |
| 4,732,154 | 3/1988 | Shiber | 606/159 |
| 4,798,591 | 1/1989 | Okada | 604/164 |
| 4,846,193 | 7/1989 | Tremulis et al. | 128/772 |
| 4,877,037 | 10/1989 | Ko et al. | 128/756 |
| 4,946,440 | 8/1990 | Hall | 604/95 |
| 4,966,162 | 10/1990 | Wang | 128/750 |
| 4,973,313 | 12/1990 | Katsaros et al. | 604/165 |
| 4,981,143 | 1/1991 | Sakita et al. | 128/757 |
| 5,009,659 | 4/1991 | Hamlin et al. | 606/159 |
| 5,031,634 | 7/1991 | Simon | 128/754 |

OTHER PUBLICATIONS

Foutch et al., "Endoscopic Retrograde Wire-Guided Brush . . . " *The American Journal of Gastroentenology* vol. 85, No. 7 (1990) pp. 791-795.

Venu et al., "Endoscopic Retrograde Brush Cytology: A New Technique", *Gastroenterology*, vol. 99, pp. 1457-1479, 1990.

Foutch et al., "Endoscopic Retrograde Wire-Guided Brush Cytology for Diagnosis of Patients With Malignant Obstruction of the Bile Duct", Gastroentestinal Endocscopi, vol. 35, No. 3, 1989.

*Primary Examiner*—Max Hindenburg
*Assistant Examiner*—Guy V. Tucker
*Attorney, Agent, or Firm*—Sterne, Kessler, Goldstein & Fox

[57] ABSTRACT

A wire-guided cytology brush is disclosed. The brush comprises a flexible outer sheath and a flexible inner sheath. The inner sheath is disposed within the lumen of the outer sheath. A means for collecting a tissue sample is disposed at a distal end of the inner sheath, a first handle is disposed at a proximal end of the inner sheath, and a second handle is disposed at a proximal end of the outer sheath.

The inner and outer sheaths are inserted over a guide-wire such that the guide-wire passes through the lumen of the inner sheath. A retainer clip maintains the relative positioning of the inner sheath within the outer sheath during insertion and removal of the brush assembly over the guide wire.

12 Claims, 4 Drawing Sheets

WIRE-GUIDED CYTOLOGY BRUSH

FIELD OF THE INVENTION

This invention relates generally to a brush for obtaining cytologic samples. More specifically, the invention relates to a flexible cytology brush housed in a protective sheath, wherein the entire brush assembly may be passed over a guide-wire and into position and brushing accomplished without removal of the guide-wire.

BACKGROUND OF THE INVENTION

If is often difficult to determine a benign from a malignant stricture in the biliary and/or pancreatic ductal systems, as well as in the urinary tract. Endoscopic retrograde cholangiopancreatography (ERCP) or transhepatic cholangiography (THC) in the biliary tree and retrograde cystography in the urinary tract are helpful in determining abnormalities, however, it is difficult to discern benign inflammatory conditions from malignancies using these methods. Because it is important that a clear distinction be made, a definitive diagnosis ultimately requires sampling of tissue from the stricture.

A variety of procedures may be used for tissue sample acquisition. These techniques include percutaneous needle aspiration under CAT (Computerized Axial Tomography) or ultrasound guidance, T-tube aspiration of bile or pancreatic juice, percutaneous transhepatic or transpapillary catheter aspiration during ERCP, transhepatic or transpapillary scrape biopsy, and percutaneous biopsy using a biopsy gun. Some of these techniques are time consuming and/or tedious, and further, the diagnostic yield is poor.

Brush cytology has been shown to reliably diagnose a malignant stricture with a sensitivity of about fifty percent. However, standard brush cytology is often difficult or impossible to perform.

One of the known brushing techniques for biliary or pancreatic strictures involves placing a guide-wire across the stricture in question. Usually, the guide-wire is already in position following ERCP. A catheter or sheath is then fed along the guide-wire and into position at the proximal end of the stricture. The guide-wire is then removed from the catheter and the cytology brush is then inserted into the catheter and advanced to the site of the stricture. Once the brush exits the distal end of the catheter, brushing of the suspect lesion can be performed by repetitive push/pull manipulation of the proximal end of the brush. The brush is then withdrawn from the catheter and the guide-wire re-inserted.

This known brushing method suffers from several shortcomings. First, withdrawal of the brush through the catheter results in some, if not most of the sample being lost along the surface of the catheter during the withdrawal. Secondly, removal and re-insertion of the guide-wire is a tedious and time consuming process. Further, re-insertion of the guide-wire may be impossible due to tissue swelling and, as a result, access to the biliary or pancreatic duct may be lost.

If brushing could be performed without removal of the guide-wire, cytologic sampling could be performed more swiftly, accurately, and without the risk of losing access to the duct above the stricture.

SUMMARY OF THE INVENTION

A wire-guided cytology brush is disclosed. The brush comprises a flexible outer sheath and a flexible inner sheath. The inner sheath is disposed within the lumen of the outer sheath. A plurality of brushing elements are disposed at a distal end of the inner sheath, a first handle is disposed at a proximal end of the inner sheath, and a second handle is disposed at a proximal end of the outer sheath.

The concentrically disposed sheaths are inserted over a guide-wire such that the guide-wire passes through the lumen of the inner sheath. The brush assembly is inserted into position for cytologic brushing (e.g., of a pancreatic or biliary duct stricture). Brushing is accomplished by manipulating the handles such that the brushing elements disposed on the inner sheath are extended outward from a distal end of the outer sheath and into contact with the stricture.

In one aspect of the invention, a retainer clip maintains the relative positioning of the inner sheath within the outer sheath during insertion and removal of the brush assembly over the guide wire.

It is an advantage of the present invention that a sheathed cytology brush may be passed over a guide-wire, brushing can be accomplished, and the entire brush assembly can be withdrawn without removal of the guide-wire and without loss of the tissue sample.

PREFERRED EMBODIMENT OF THE INVENTION

Figure 1:
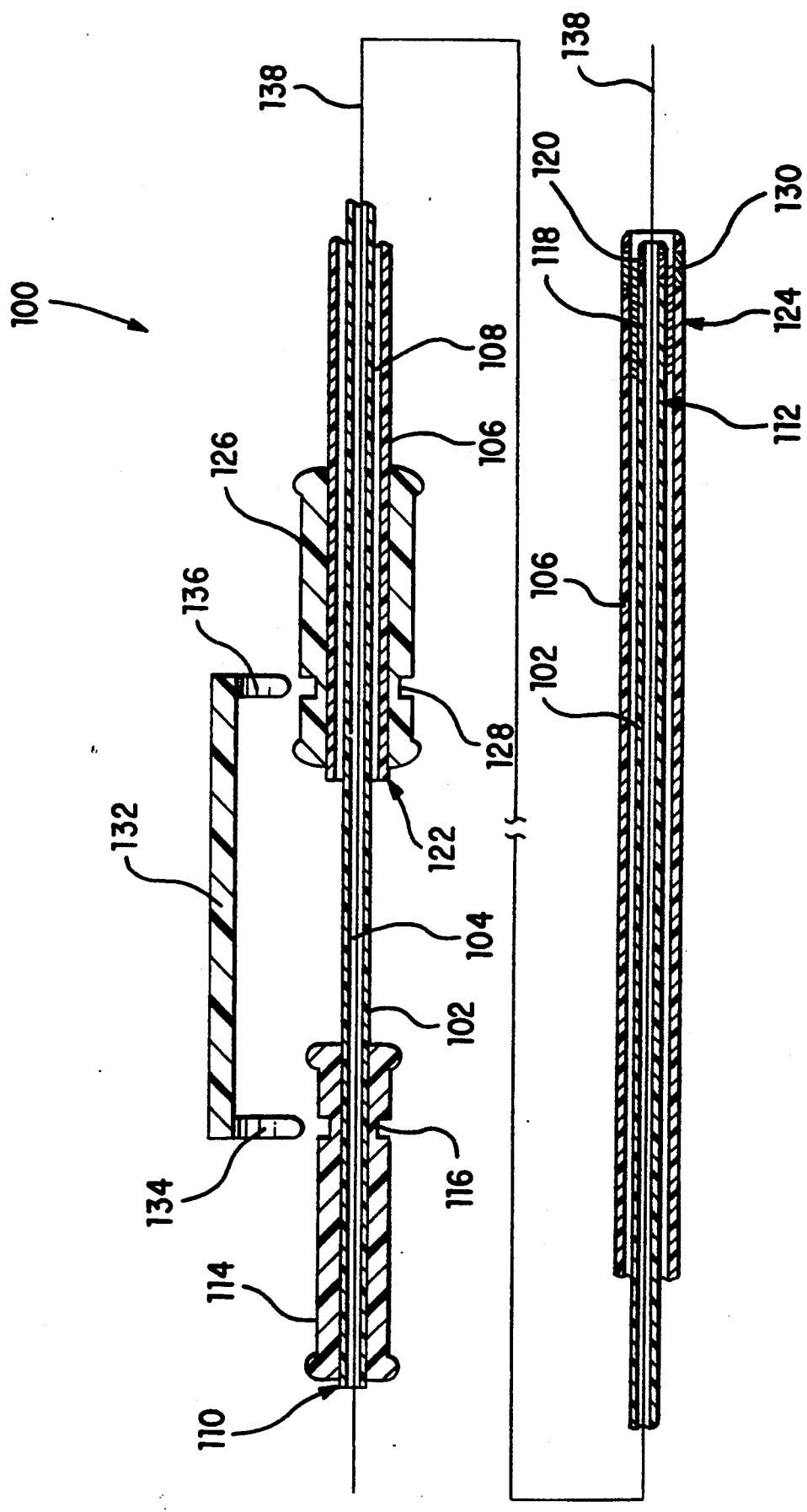
FIG. 1 is a cross-sectional diagram of the wire-guided cytology brush of the present invention shown in the retracted position.

Referring to FIGS. 1-5, the preferred embodiment of the present invention for use through a side-viewing duodenoscope (for ERCP) is discussed. Cytology brush 100 comprises a thin-walled, flexible inner tube or sheath 102 having a hollow center or lumen 104 and a thin-walled flexible outer tube or sheath 106 having a hollow center or lumen 108. Inner sheath 102 is concentrically disposed within lumen 108 of outer sheath 106. Sheaths 102 and 106 are made from TEFLON, a material made by DuPont de Nemours and Co., or an equivalent material which is flexible and will provide a low coefficient of friction between sheaths 102 and 106.

Inner sheath 102 has an outer diameter which is less than the inner diameter of lumen 108 of outer sheath 106 such that inner sheath 102 can be freely moved longitudinally within lumen 108 of outer sheath 106. Inner sheath 102 has a proximal end 110 and a distal end 112. A first handle 114 is fixedly attached to the outer surface of inner sheath 102 at proximal end 110. Handle 114 has a circumferential groove 116 formed in its outer surface. A plurality of brushing elements 118 and an inner radiographic marker 120 are disposed at the distal end 112 of inner sheath 102.

Outer sheath 106 has a proximal end 122 and a distal end 124. A second handle 126 is fixedly attached to the outer surface of outer sheath 106 at proximal end 122. Handle 126 has a circumferential groove 128 formed in its outer surface. An outer radiographic marker 130 is disposed at the distal end 124 of outer sheath 106.

Radiographic markers 120 and 130 are thin laminates fixedly attached to the surface of sheaths 102 and 106 respectively. Each includes a radio-opaque material (e.g., lead) which is highly discernable relative to living tissue when viewed under a fluoroscope. Used in conjunction with a fluoroscope, markers 120 and 130 facilitate proper positioning of cytology brush 100 along guide wire 138.

A retainer clip 132 has a first end 134 and a second end 136. First clip end 134 has a substantially circular opening of a diameter suitable for coupling with groove 116 in first handle 114. Similarly, second clip end 136 has a substantially circular opening of a diameter suitable for coupling with groove 128 in second handle 126.

Clip 132, including clip ends 134 and 136, is of unitary molded construction and is made from a resilient material such as a plastic. This allows clip ends 134 and 136 to deform so that the openings can accept handles 114 and 126 when ends 134 and 136 are urged upon grooves 116 and 128 respectively. When clip 132 is in position, the resilient clip ends resume their pre-deformed shapes and close upon grooves 116 and 128 causing clip 132 to "snap" into position. Thereby, clip 132 secures sheaths 102 and 106 in a fixed relative position with distal end 112 of inner sheath 102 retracted into distal end 124 of outer sheath 106 as shown in FIG. 1

Cytology brush 100 may have the following approximate dimensions. The overall length of brush 100 is 200 cm in the retracted position (i.e., with Inner sheath 102 is 8-10 cm longer than outer sheath 106. Handles 114 and 126 are each 3-5 cm long. These dimensions allow distal end 112 of inner sheath 102 to extend 3-7 cm out from the distal end 124 of outer sheath 106. In this extended position, handles 114 and 126 abut one another and limit further extension of inner sheath 102 outward from distal end 124 of outer sheath 106.

The diameter of outer sheath 106 should be of a size which can be easily passed through the instrument channel of known endoscopes. For example, a diameter of 3 mm could be used with a side-viewing duodenoscope having an instrument port diameter of 3.2 mm.

The diameter of inner sheath 102 should be substantially less than the diameter of outer sheath 106 so that inner sheath 102 can be maneuvered longitudinally within outer sheath 106 with minimum frictional resistance. Concurrently, the diameter of inner sheath 102 should be large enough to allow a guide-wire to be passed through lumen 104 of inner sheath 102 with minimum frictional resistance. In the preferred embodiment, lumen 104 should be able to accommodate a standard 0.9 mm (0.035') guide-wire.

Figure 2:
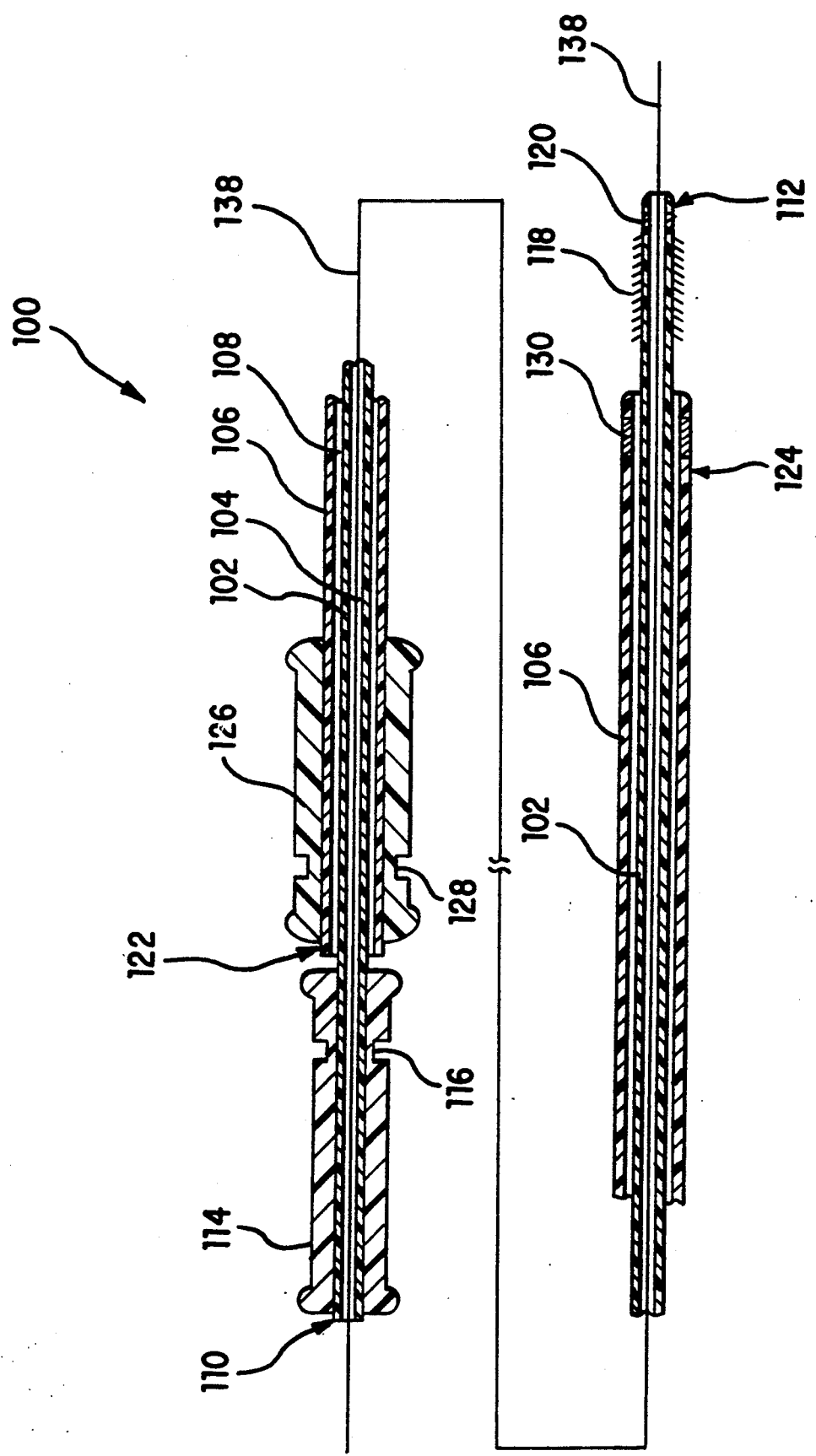
FIG. 2 is a cross-sectional diagram of the wire-guided cytology brush of the present invention shown in the extended position.
Figure 3:
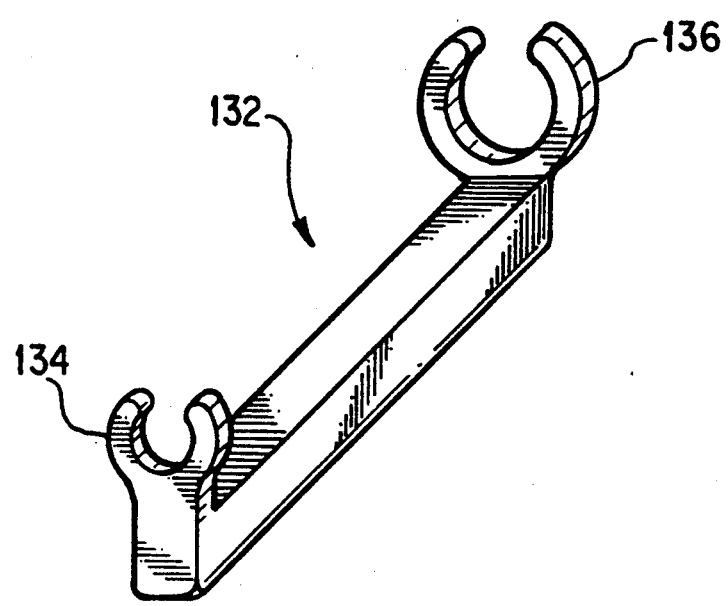
FIG. 3 is a perspective view of retainer clip 132.
Figure 5:
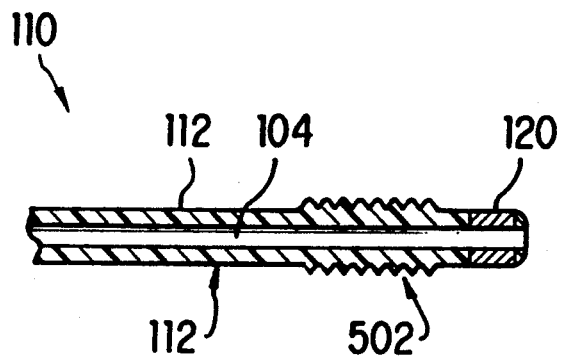
FIG. 5 is a cross-sectional diagram of the distal end 112 of the inner sheath 110 in an alternate embodiment in which a plurality of ridges 502 are substituted for brushing elements 118.
Figure 4:
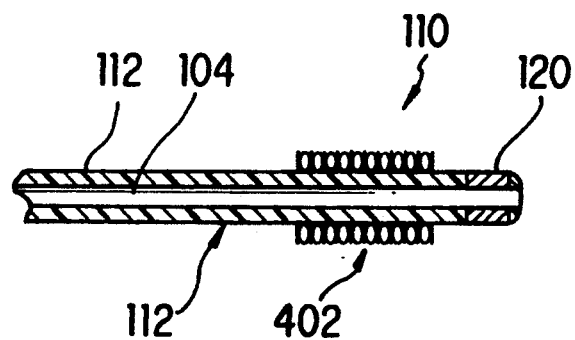
FIG. 4 is a cross-sectional diagram of the distal end 112 of the inner sheath 110 in an alternate embodiment in which a plurality of loops 402 are substituted for brushing elements 118.

Brushing elements 118 are disposed on inner sheath 102 for a length of 1-2 cm, and extend 1-2 mm radially outward from inner sheath 102. Brushing elements 118 may be bristles, (as shown in FIGS. 1 and 2) loops (as shown in FIG. 4), ridges (as shown in FIG. 5), corrugations, or alternatively, any scraping collection device. Brushing elements 118 may be made from known material and fixedly attached to the surface of inner sheath 102 or, alternatively, they may be inherently formed on the surface of inner sheath 102.

Operation of brush 100 is as follows. With clip 132 in position, brushing elements 118 are protected within outer sheath 106 and brush 100 is ready for insertion. Guide-wire 138 remains positioned across the stricture following ERCP so that the proximal end of the guide-wire, which exits the biopsy port of the endoscope, is fed into lumen 104 of inner sheath 102 at distal end 112. Cytology brush 100 is then pushed over guide-wire 138 and into the duct to the level of the stricture. This procedure may be monitored by fluoroscopy using radiographic markers 120 and 130.

Once brush assembly 100 is properly positioned with respect to the stricture, clip 132 is removed from grooves 116 and 128 such that relative motion can be imparted between handles 114 and 126. Manipulating these handles, the distal end 112 of inner sheath 102 can be extended from the distal end 124 of outer sheath 106 (as shown in FIG. 2) such that brushing elements 118 are exposed to the stricture. Handle 114 can then be manipulated in a back and forth motion so that brushing elements 118 make multiple contacts with the stricture. Thereby, cells from the stricture are scraped off and attached to brushing elements 118.

Once the specimen is collected, brushing elements 118 are again retracted into outer sheath 106 and clip 132 is coupled with handles 114 and 126 to fix their relative positions. With the guide-wire still in place, brush 100 is withdrawn back over the guide-wire and out of the patient. The cytology sample obtained in this manner is then removed from brushing elements 118 and smeared onto a glass slide for fixing in the usual manner.

Because guide-wire 138 is left in place after brushing, it is readily available for other procedures such as stent placement. Further, because the position of inner sheath 102 (and corresponding brushing elements 118) is fixed with respect to outer sheath 106, sample loss from brushing elements 118 is minimized during withdrawal of brush 100.

Cytology brush 100 is contemplated to be relatively inexpensive to manufacture such that it (or a portion of it) may be disposable. That is, it may be disposed of after a single use. If a reusable embodiment is desired, then the materials of construction should be chosen accordingly to allow either autoclaving or gas sterilization.

In addition to being useful in the performance of cytologic brushing during ERCP's, this novel brush may be used in any setting which uses a guide-wire and requires cytologic sampling. For example, in addition to the biliary and pancreatic systems, a urologist may use this new brush for brushing of strictures in the ureters of the urinary tract, and a radiologist may use it for his invasive procedures involving the bile ducts.

For applications in urology or radiology, brush 100 could be modified to suit the specific application at hand. For example, urology might require that brush 100 be much shorter in length and possibly thicker in diameter than the brush used for ERCP.

Although the invention has been described and illustrated with a certain degree of particularity, it is understood that those skilled in the art will recognize a variety of applications and appropriate modifications within the spirit of the invention and the scope of the claims.

What is claimed is:

1. A cytology brush comprising:
    a guide wire;
    a first, flexible sheath having a proximal end and a distal end, said first sheath defining a first lumen having a first opening in said proximal end and a second opening in said distal end;

a second, flexible sheath having a proximal end and a distal end, said second sheath defining a second lumen having a third opening in said proximal end and a fourth opening in said distal end, said second sheath being disposed in said first lumen of said first sheath and being adapted for longitudinal movement therethrough such that said distal end of said second sheath may be extended out through said second opening of said first sheath, said second sheath allowing free passage of the guide-wire through said second lumen; and a plurality of brushing elements disposed on said second sheath at said distal end such that said brushing elements are extendable out from and retractable into said first lumen with said distal end of said second sheath.

2. A cytology brush as set forth in claim 1, wherein said first sheath further comprises a first handle fixedly attached to the outer surface of said first sheath at its proximal end.

3. A cytology brush as set forth in claim 2, wherein said second sheath further comprises a second handle fixedly attached to the outer surface of said second sheath at its proximal end.

4. A cytology brush as set forth in claim 3, further comprising:
a retainer clip having a first end adapted for attachment to said first handle and a second end adapted for attachment to said second handle, said retainer clip capable of securing the relative longitudinal positioning of said second sheath within said first sheath.

5. A cytology brush as set forth in claim 4, wherein said first sheath further comprises a radiographic marker disposed at the distal end of said first sheath.

6. A cytology brush as set forth in claim 5, wherein said second sheath further comprises a radiographic marker disposed at the distal end of said second sheath.

7. A cytology brush as set forth in claim 4, wherein said brushing elements comprise bristles.

8. A cytology brush as set forth in claim 4, wherein said brushing elements comprise loops.

9. A cytology brush as set forth in claim 4, wherein said brushing elements comprise ridges.

10. A cytology brush comprising:
a guide wire;
a flexible inner tube having a proximal end opening at a proximal end and a distal end opening at a distal end, and having a plurality of brushing elements disposed at said distal end of said inner tube and a first handle fixedly attached to the proximal end of said inner tube, said inner tube having an inner diameter which is large enough to allow passage of the guide-wire therethrough;

a flexible outer tube having a proximal end opening at a proximal end and a distal end opening at a distal end, and having a second handle fixedly attached to the proximal end of said outer tube, said outer tube having an inner diameter which is greater than an outer diameter of said inner tube such that said inner tube may be passed longitudinally through said outer tube and said distal end of said inner tube may be selectively extended out from and retracted into said distal end opening of said outer tube by imparting relative motion to said first and second handles; and a retainer clip adapted for attachment to said first and second handles whereby the longitudinal position of said first handle relative to said second handle may be fixed.

11. A method for collecting a sample of tissue from any of the various ductal systems of living body, the method comprising the following steps:
(a) introducing a guide-wire into the living body and into close proximity to the tissue to be sampled;
(b) passing a cytology brush over said guide-wire until a distal end of said cytology brush is in close proximity to the tissue to be sampled, said cytology brush including an outer flexible sheath and an inner flexible sheath, said inner and outer flexible sheaths each having a distal end and a proximal end, said outer flexible sheath having a first lumen open at both ends, said inner flexible sheath disposed in said first lumen of said outer flexible sheath, said inner flexible sheath having a second lumen open at both ends and adapted to accept passage of said guide-wire therethrough, said inner sheath further having a means for collecting a tissue sample connected to said distal end of said inner sheath;
(c) extending said distal end of said inner sheath out from said first lumen of said outer sheath such that said means for collecting a tissue sample si brought into contact with the tissue to be sampled;
(d) retracting said distal end of said inner sheath back into said lumen of said outer sheath such that said means for collecting a tissue sample is shielded by said outer sheath; and
(e) withdrawing the cytology brush over said guide-wire from the living body without substantially disturbing the position of said guide-wire.

12. The method of claim 11, further comprising a step between steps (c) and (d) of:
(f) manipulating said proximal ends of said inner sheath and said outer sheath with a push/pull movement such that said means for collecting is brought into multiple contact with the tissue to be sampled.

* * * * *